(12) United States Patent
Hanbury

(10) Patent No.: US 11,400,252 B2
(45) Date of Patent: Aug. 2, 2022

(54) NON-PHARMACEUTICAL METHOD OF MANAGING PAIN

(71) Applicant: SANA HEALTH, INC., Lafayette, CO (US)

(72) Inventor: Richard Hanbury, Lafayette, CO (US)

(73) Assignee: SANA HEATH INC., Lafayette, CO (US)

( * ) Notice: Subject to any disclaimer, the term of this patent is extended or adjusted under 35 U.S.C. 154(b) by 0 days.

(21) Appl. No.: 16/418,561

(22) Filed: May 21, 2019

(65) Prior Publication Data

US 2019/0374742 A1 Dec. 12, 2019

Related U.S. Application Data

(63) Continuation-in-part of application No. 15/360,808, filed on Nov. 23, 2016, now Pat. No. 10,328,236.

(60) Provisional application No. 62/675,280, filed on May 23, 2018, provisional application No. 62/258,965, filed on Nov. 23, 2015.

(51) Int. Cl.
*A61M 21/02* (2006.01)
*A61M 21/00* (2006.01)

(52) U.S. Cl.
CPC ....... *A61M 21/02* (2013.01); *A61H 2205/027* (2013.01); *A61M 2021/0027* (2013.01); *A61M 2021/0044* (2013.01)

(58) Field of Classification Search
CPC .......... A61M 21/02; A61M 2021/0027; A61M 2021/0044; A61M 2230/005; A61M 2230/06; A61M 2230/10; A61M 2230/18; A61M 2230/30; A61M 2230/50; A61M 2230/60; A61M 2021/0022; A61M 21/00; A61M 2205/3306; A61M 2205/507; A61H 2205/027; A61N 2005/0647; A61N 5/0613; A61N 5/0618
See application file for complete search history.

(56) References Cited

U.S. PATENT DOCUMENTS 4,172,406 A 10/1979 Martinez
4,315,502 A 2/1982 Gorges
(Continued)

FOREIGN PATENT DOCUMENTS

CN 205814527 U 12/2016
CN 104546285 B 3/2017
(Continued)

OTHER PUBLICATIONS

The International Searching Authority, Notification of Transmittal of the International Search Report and the Written Opinion of the International Searching Authority dated Aug. 2, 2019 in International Application No. PCT/US19/033322, 19 pages.
(Continued)

*Primary Examiner* — Amanda K Hulbert
(74) *Attorney, Agent, or Firm* — Dickinson Wright PLLC; Stephen A. Mason; Jonathan A. Schnayer

(57) ABSTRACT

A method of managing pain provides sensory stimuli to a person. The sensor stimuli include visual and/or auditory stimuli which are pulsed at the rate of various types of brain waves. The method is applicable for treating nociceptive or neuropathic pain and/or for improving the person's tolerance for pain. Treatment is provided for approximately 15 minutes using a portable headset.

32 Claims, 9 Drawing Sheets

(56) References Cited

U.S. PATENT DOCUMENTS

| | | | |
|---|---|---|---|
| 4,892,106 | A | 1/1990 | Gleeson |
| 4,966,164 | A | 10/1990 | Colsen et al. |
| 5,343,261 | A | 8/1994 | Wilson |
| 5,783,909 | A | 7/1998 | Hochstein |
| 6,123,661 | A | 9/2000 | Fukushima et al. |
| 6,409,655 | B1 | 6/2002 | Wilson et al. |
| 8,562,659 | B2 | 10/2013 | Wells et al. |
| 8,838,247 | B2 | 9/2014 | Hagedorn et al. |
| 8,852,073 | B2 | 10/2014 | Genereux et al. |
| 8,932,199 | B2 | 1/2015 | Berka et al. |
| D775,260 | S | 12/2016 | Gordon et al. |
| 9,649,469 | B2 | 5/2017 | Hyde et al. |
| D805,515 | S | 12/2017 | Bowes et al. |
| D827,701 | S | 9/2018 | Nguyen et al. |
| 10,328,236 | B2 | 6/2019 | Hanbury |
| 10,383,769 | B1 | 8/2019 | Miller |
| 10,449,326 | B2 | 10/2019 | Genereux et al. |
| 2002/0198577 | A1 | 12/2002 | Jaillet |
| 2006/0106276 | A1 | 5/2006 | Shealy et al. |
| 2006/0252979 | A1 | 11/2006 | Vesely et al. |
| 2008/0269629 | A1* | 10/2008 | Reiner ........... A61B 5/4836 600/544 |
| 2009/0156886 | A1 | 6/2009 | Burgio et al. |
| 2010/0056854 | A1* | 3/2010 | Chang ............ A61M 21/00 600/28 |
| 2010/0161010 | A1* | 6/2010 | Thomas .......... A61M 21/00 607/88 |
| 2010/0323335 | A1 | 12/2010 | Lee |
| 2011/0075853 | A1* | 3/2011 | Anderson ....... A61B 5/11 381/60 |
| 2011/0213664 | A1 | 9/2011 | Osterhout et al. |
| 2011/0257712 | A1 | 10/2011 | Wells et al. |
| 2012/0095534 | A1* | 4/2012 | Schlangen ...... H05B 47/16 607/90 |
| 2012/0211013 | A1* | 8/2012 | Otis .............. A61M 21/02 128/898 |
| 2013/0035734 | A1* | 2/2013 | Soler Fernnndez ........ A61N 1/36021 607/3 |
| 2013/0225915 | A1 | 8/2013 | Redfield et al. |
| 2013/0267759 | A1* | 10/2013 | Jin ............... A61N 2/004 600/9 |
| 2013/0303837 | A1 | 11/2013 | Berka et al. |
| 2014/0336473 | A1 | 11/2014 | Greco |
| 2015/0231395 | A1* | 8/2015 | Saab ............. A61N 1/36071 607/46 |
| 2015/0268673 | A1* | 9/2015 | Farzbod ......... H04R 1/1008 700/280 |
| 2016/0228771 | A1 | 8/2016 | Watson |
| 2017/0143935 | A1 | 5/2017 | Hanbury |
| 2017/0189639 | A1 | 7/2017 | Mastrianni |
| 2017/0252532 | A1 | 9/2017 | Holsti et al. |
| 2017/0312476 | A1 | 11/2017 | Woo |
| 2018/0184969 | A1 | 7/2018 | Zhao et al. |
| 2018/0250494 | A1 | 9/2018 | Hanbury |
| 2019/0030279 | A1 | 1/2019 | Nowlin |
| 2019/0192077 | A1 | 6/2019 | Kaiser et al. |
| 2019/0262576 | A1 | 8/2019 | Mastrianni |
| 2019/0388020 | A1 | 12/2019 | Stauch et al. |
| 2020/0139112 | A1 | 5/2020 | Aharonovitch |
| 2020/0268341 | A1 | 8/2020 | Stroman |
| 2020/0368491 | A1 | 11/2020 | Poltorak |
| 2021/0008332 | A1 | 1/2021 | Jin et al. |

FOREIGN PATENT DOCUMENTS

| | | |
|---|---|---|
| WO | 2001064005 A2 | 9/2001 |
| WO | 2012117343 A1 | 9/2012 |
| WO | 2015028480 A1 | 3/2015 |
| WO | 2016140408 A1 | 9/2016 |
| WO | 2019060598 A1 | 3/2019 |
| WO | 2020219350 A1 | 10/2020 |

OTHER PUBLICATIONS

International Searching Authority, Search Report and Written Opinion in PCT/US2020/019091, dated May 6, 2020; 13 pages.

European Patent Office, Supplementary European Search Report dated Jun. 5, 2019 for European Patent Application No. 16869299.4, eight pages.

Chinnakkaruppan Adaikkan, et al., "Gamma Entrainment Binds Higher-Order Brain Regions and Offers Neuroprotection", Neuron, https://linkinghub.elsevier.com/retrieve/pii/S0896627319303460, May 7, 2019 (May 7, 2019), 18 Pages.

Liviu Aron, et al., "Neural synchronization in Alzheimer's disease", Nature, Journal, vol. 540, Dec. 7, 2016 (Dec. 7, 2016), pp. 207-208.

Pam Belluck, "Could simply listening to this sound help cure Alzheimer's disease? MIT researchers are investigating", Boston Globe, https://www.bostonglobe.com/news/science/2019/03/14/could-simply-listening-this-sound-help-cure-alzheimer-disease-mit-researchers-are-investigating/2npZrAp8g9kLSfURbTxaVO/story.html, Mar. 14, 2019 (Mar. 14, 2019), 4 Pages.

Pam Belluck, "A Possible Alzheimer's Treatment With Clicks and Flashes? It Worked on Mice", New York Times, https://www.nytimes.com/2019/03/14/health/alzheimers-memory.html, Mar. 14, 2019 (Mar. 14, 2019), 5 Pages.

Angus Chen, "An Hour of Light and Sound a Day Might Keep Alzheimer's at Bay", Scientific American, https://www.scientificamerican.com/article/an-hour-of-light-and-sound-a-day-might-keep-alzheimers-at-bay/, Mar. 14, 2019 (Mar. 14, 2019), 5 Pages.

Aimee Corso, "Cognito Therapeutics Launched with Exclusive License to Promising Alzheimer's Research from The Massachusetts Institute of Technology", Business Wire, Boston and San Francisco, https://www.businesswire.com/news/home/20161207006042/en/Cognito-Therapeutics-Launched-Exclusive-License-Promising-Alzheimer%E2%80%99s, Dec. 7, 2016 (Dec. 7, 2016), 3 Pages.

Hannah Devlin, "Strobe lighting provides a flicker of hope in the fight against Alzheimer's", The Guardian, https://www.theguardian.com/science/2016/dec/07/strobe-lighting-provides-a-flicker-of-hope-in-the-fight-against-alzheimers, Dec. 7, 2016 (Dec. 7, 2016), 3 Pages.

Jamie Ducharme, "The End of Alzheimer's?", Boston, Magazine, https://www.bostonmagazine.com/health/2017/11/27/li-huei-tsai-alzheimers-treatment/, Nov. 27, 2017 (NOv. 7, 2017), 4 Pages.

Damian Garde, "'Beyond amyloid': A look at what's next in Alzheimer's research", STAT, https://www.statnews.com/2017/08/18/beyond-amyloid-alzheimers-research/, Aug. 18, 2017 (Aug. 18, 2017), 5 Pages.

Melissa Healy, "Flickering lights may illuminate a path to Alzheimer's treatment", Los Angeles Times, Dec. 7, 2016 (Dec. 7, 2016), 8 Pages.

Mathan Hurst, "Could Flickering Lights Help Treat Alzheimer's?", Smithsonian, https://www.smithsonianmag.com/innovation/could-flickering-lights-help-treat-alzheimers-180961762/, Jan. 11, 2017 (Jan. 11, 2017), 2 Pages.

Hannah F. Iaccarino, et al., "Gamma frequency entrainment attenuates amyloid load and modifies microglia", Mature, Journal, vol. 540, Dec. 7, 2016 (Dec. 7, 2016), pp. 230-235.

Anthony J. Martorell, et al., "Multi-sensory Gamma Stimulation Ameliorates Alzheimer's-Associated Pathology and Improves Cognition", Cell, https://www.cell.com/cell/fulltext/S0092-8674(19)30163-1, Mar. 14, 2019 (Mar. 14, 2019), 16 Pages.

Helen Thomson, "How flashing lights and pink noise might banish Alzheimer's, improve memory and more", Nature, https://www.nature.com/articles/d41586-018-02391-6, Feb. 28, 2018 (Feb. 28, 2018), 10 Pages.

Meg Tirrell, "Could flashing light treat Alzheimer's? Fresh approaches to treating the disease", CNBC, https://www.cnbc.com/2017/03/29/could-flashing-light-treat-alzheimers-fresh-approaches-to-treating-the-disease.html, Mar. 29, 2017 (Mar. 29, 2017), 6 Pages.

Anne Trafton, "Ed Boyden receives 2018 Canada Gairdner International Award", McGovern Institute, https://mcgovern.mit.edu/2018/03/27/ed-boyden-receives-2018-canada-gairdner-international-award/, Mar. 27, 2018 (Mar. 27, 2018), 3 Pages.

(56) References Cited

OTHER PUBLICATIONS

Molly WEBSTER, et al., "Bringing Gamma Back", WNYC Studios, https://www.wnycstudios.org/story/bringing-gamma-back, Dec. 8, 2016 (Dec. 8, 2016), 3 Pages.

Robert Weisman, "MIT team uses LEDs to attack Alzheimer's", Boston Globe, https://www.bostonglobe.com/business/2016/12/07/led-technology-from-mit-used-startup-working-alzheimer-treatment/Kbdjp9WvfoPLfC1bNhvGOI/story.html, Dec. 7, 2016 (Dec. 7, 2016), 4 Pages.

Nicole Wetsman, "Flickering light seems to help mice with Alzheimer's-like symptoms", Popular Science, https://www.popsci.com/flickering-light-genes-alzheimers, May 7, 2019 (May 7, 2019), 2 Pages.

Ed Yong, "Beating Alzheimer's With Brain Waves", The Atlantic, https://www.theatlantic.com/science/archive/2016/12/beating-alzheimers-with-brain-waves/509846/, Dec. 7, 2016 (Dec. 7, 2016), 8 Pages.

Nstc, "First Friday Biosciences: Nov. 3 in Woburn", https://www.nstc.org/previous-events/first-friday-biosciences-nov-3-in-woburn/, Nov. 3, 2017 (Nov. 3, 2017), 8 Pages.

The Picower Institute, "Tsai earns Hans Wigzell Research Foundation Science Prize", https://picower.mit.edu/news/tsai-earns-hans-wigzell-research-foundation-science-prize, Jan. 23, 2019 (Jan. 23, 2019), 3 Pages.

PCT Search Report and Written Opinion, dated May 7, 2018 in International Application PCT/US2018020547, filed Mar. 1, 2018, 10 pages.

PCT Search Report and Written Opinion, dated Feb. 3, 2017 in International Application PCT/US2016063651, filed Nov. 23, 2016, 13 pages.

International Searching Authority, Search Report and Written Opinion in PCT/US20/41423, dated Oct. 9, 2020; 9 pages.

European Patent Office, Extended European Search Report dated Nov. 27, 2020 for European Patent Application No. 18761087.8, 9 pages.

Illumy by Sound Oasis; https://www.soundoasis.com/products/light-therapy/illumy-the-smart-sleep-mask/; Product description downloaded Aug. 2, 2021; 6 pages Copyright 2000-2021 AvivaHealth.com.

Remee Lucid Dreaming Mask; http://sleepwithremee.com/; Product description downloaded Aug. 3, 2021; 10 pages Copyright 2018 Bitbanger LLC.

Lumos Smart Sleep Mask; https://lumos.tech/lumos-smart-sleep-mask/; Product description downloaded Aug. 3, 2021; 3 pages.

Dreamlight Zen; https://dreamlight.tech/products/dreamlight-zen; product description downloaded Aug. 3, 2021; 16 pages; Copyright 2021 Dreamlight.

Ntellectual Property India, Examination Report for Application No. 201837022885, dated May 6, 2021; 7 pages.

Szafir, et al., Pay Attention Designing Adaptive Agents that Monitor and Improve User Engagement, Conference on Human Factors in Computing Systems, May 5, 2012, 10 Pages.

International Search Report and Written Opinion in PCT/US2021/032260, dated Aug. 31, 2021; 9 pages.

\* cited by examiner

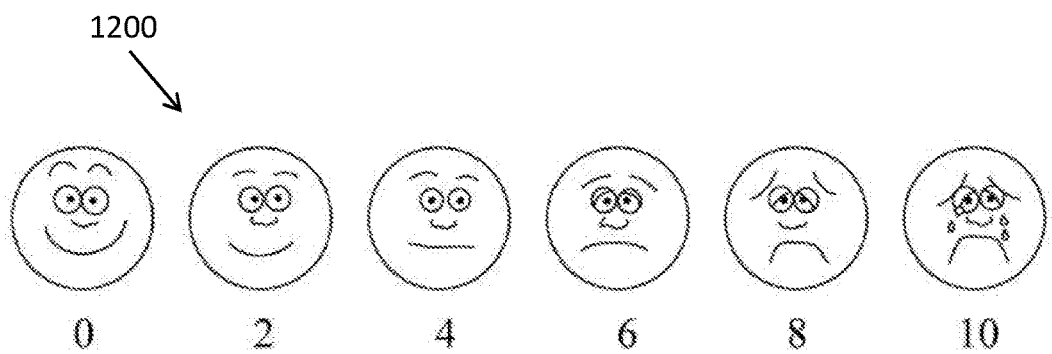
FIG. 12 (New)

500

| Segments A1-A4 for 120s | Auditory Left | Auditory Right | Light Left | Light Right |
|---|---|---|---|---|
| Segment A1 (Light and Auditory both sides pulse together) Repeat 116 times, followed by 0.5 sec gap | On 0.1277 sec | On 0.1277 sec | On 0.1277 sec | On 0.1277 sec |
| | Off 0.1277 sec | Off 0.1277 sec | Off 0.1277 sec | Off 0.1277 sec |
| Segment A2 (light and auditory on left side, alternating light and auditory on right). Repeat 116 times, followed by 0.5 sec gap | On 0.1277 sec | Off 0.1277 sec | On 0.1277 sec | Off 0.1277 sec |
| | Off 0.1277 sec | On 0.1277 sec | Off 0.1277 sec | On 0.1277 sec |
| Segment A3 (both lights together, alternating with both auditory signals together) Repeat 115 times, followed by 0.5 sec gap | On 0.1277 sec | On 0.1277 sec | Off 0.1277 sec | Off 0.1277 sec |
| | Off 0.1277 sec | Off 0.1277 sec | On 0.1277 sec | On 0.1277 sec |
| Segment A4 (auditory left and light right together, alternating auditory right and light left together) Repeat 115 times, followed by 0.5 sec gap | On 0.1277 sec | Off 0.1277 sec | Off 0.1277 sec | On 0.1277 sec |
| | Off 0.1277 sec | On 0.1277 sec | On 0.1277 sec | Off 0.1277 sec |

FIG. 5

| Segments B1-B4 for 120s | Auditory Left | Auditory Right | Light Left | Light Right |
|---|---|---|---|---|
| Segment B1 (Light and Auditory both sides pulse together) Repeat 45 times, followed by 0.5 sec gap | On 0.3333 sec | On 0.3333 sec | On 0.3333 sec | On 0.3333 sec |
| | Off 0.3333 sec | Off 0.3333 sec | Off 0.3333 sec | Off 0.3333 sec |
| Segment B2 (light and auditory on left side, alternating light and auditory on right) Repeat 44 times, followed by 0.5 sec gap | On 0.3333 sec | Off 0.3333 sec | On 0.3333 sec | Off 0.3333 sec |
| | Off 0.3333 sec | On 0.3333 sec | Off 0.3333 sec | On 0.3333 sec |
| Segment B3 (both lights together, alternating with both auditory signals together) Repeat 44 times, followed by 0.5 sec gap | On 0.3333 sec | On 0.3333 sec | Off 0.3333 sec | Off 0.3333 sec |
| | Off 0.3333 sec | Off 0.3333 sec | On 0.3333 sec | On 0.3333 sec |
| Segment B4 (auditory left and light right together, alternating auditory right and light left together) Repeat 44 times, followed by 0.5 sec gap | On 0.3333 sec | Off 0.3333 sec | Off 0.3333 sec | On 0.3333 sec |
| | Off 0.3333 sec | On 0.3333 sec | On 0.3333 sec | Off 0.3333 sec |

| Repeat the following Segments C1-C4 6 times for a total of 12 minutes | Auditory Left | Auditory Right | Light Left | Light Right |
|---|---|---|---|---|
| Segment C1 (Light and Auditory both sides pulse together) Repeat 15 times, followed by 1 sec gap | On 1 sec | On 1 sec | On 1 sec | On 1 sec |
| | Off 1 sec | Off 1 sec | Off 1 sec | Off 1 sec |
| Segment C2 (light and auditory on left side, alternating light and auditory on Right) Repeat 15 times, followed by 1 sec gap | On 1 sec | Off 1 sec | On 1 sec | Off 1 sec |
| | Off 1 sec | On 1 sec | Off 1 sec | On 1 sec |
| Segment C3 (both lights together, alternating with both auditory signals together) Repeat 14 times, followed by 1 sec gap | On 1 sec | On 1 sec | Off 1 sec | Off 1 sec |
| | Off 1 sec | Off 1 sec | On 1 sec | On 1 sec |
| Segment C4 (auditory left and light right together, alternating auditory right and light left together) Repeat 14 times, followed by 1 sec gap | On 1 sec | Off 1 sec | Off 1 sec | On 1 sec |
| | Off 1 sec | On 1 sec | On 1 sec | Off 1 sec |

FIG. 7

NON-PHARMACEUTICAL METHOD OF MANAGING PAIN

CROSS-REFERENCE TO RELATED APPLICATIONS

This application claims the benefit of U.S. Provisional Application No. 62/675,280, filed May 23, 2018, and is a Continuation-In-Part of U.S. patent application Ser. No. 15/360,808 filed on Nov. 23, 2016 which claims the benefit of U.S. Provisional Application No. 62/258,965 filed on Nov. 23, 2015. The contents of each of these applications are hereby incorporated by reference in their entirety.

BACKGROUND OF THE INVENTION

Field of the Invention

The present invention generally relates to the management of pain, and more particularly to a non-pharmaceutical method of managing pain.

Discussion of the Background

Pain is most commonly managed by the use of drugs. While this may be effective, it has become obvious that the opioids, for example, are highly addictive and, in the U.S., have become a leading cause of death. In addition, opioids may impair one's cognitive abilities to the point where they must limit their actions due to safety or performance concerns. Other classes of pain agents, such as NSAIDs, carry other serious health risks.

Non-pharmacological approaches to pain management are being sought to provide an alternative or partial alternative to pharmacological approaches. Non-pharmacological options for pain management include spinal manipulation, massage, Alexander Technique, psychological therapies (primarily cognitive behavioral therapy [CBT]), low-level laser therapy, ultrasound, mindfulness-based stress reduction, yoga, acupuncture, and multidisciplinary rehabilitation (MDR). While each of these techniques may provide some relief for pain, they are not generally effective.

There is a need for techniques for pain management that do not rely on drugs, that can be safely self-administered, which are useful for a wide variety of types of pain, and which do not diminish the person's ability to function and perform as a result of the treatment.

Brief Summary of the Invention

The present invention overcomes the disadvantages of the prior art by providing a non-pharmaceutical method of managing pain, either by itself or when used with pharmaceutical or other nonpharmaceutical methods.

It is one aspect of certain embodiment to provide a method of managing pain by administering a therapeutically effective amount of a sensory stimulus to the person, where said sensory stimulus includes one or more of a visual stimuli and an auditory stimuli.

It is another aspect of certain embodiments to provide a method of managing pain by administering a therapeutically effective amount of a sensory stimulus to the person, where the sensory stimulus includes two or more sensory stimuli patterns including a first stimuli pattern that is different than a second stimuli pattern.

It is another aspect of various embodiments to provide sensory stimuli that include sinusoidal components at a delta brain wave frequency, a theta brain wave frequency, or an alpha brain wave frequency.

It is yet another aspect of various embodiments to provide sensory stimuli that include sinusoidal components of between 3.75 Hz and 4.25 Hz, between 1.25 Hz and 1.75 Hz, or between 0.25 Hz and 0.75 Hz.

It is yet another aspect of certain embodiments to provide a method of managing pain by administering a therapeutically effective amount of a sensory stimulus to the person, where the sensory stimulus includes a two or more sensory stimuli patterns, including a first sensory stimuli including simultaneously providing a left visual stimuli pattern to the left eye of the user and a left auditory stimuli pattern to the left side of the head, and a second sensory stimuli including simultaneously providing a right visual stimuli pattern to the right eye of the user and a right auditory stimuli pattern to the right side of a head of the user. One or more of the left auditory stimuli pattern or the right auditory stimuli pattern comprises a sequence of stimuli patterns including the first stimuli pattern, the second stimuli pattern, and the third stimuli pattern.

It is yet another aspect of certain embodiments to provide a method of managing pain by administering a therapeutically effective amount of a sensory stimulus to the person, where the sensory stimulus includes a two or more sensory stimuli patterns, including a first sensory stimuli including simultaneously providing a left visual stimuli pattern to the left eye of the user and a right auditory stimuli pattern to the right side of the head, and a second sensory stimuli including simultaneously providing a right visual stimuli pattern to the right eye of the user and a left auditory stimuli pattern to the left side of a head of the user. One or more of the left auditory stimuli pattern or the right auditory stimuli pattern comprises a sequence of stimuli patterns including the first stimuli pattern, the second stimuli pattern, and the third stimuli pattern.

It is yet another aspect of certain embodiments to provide a method of managing pain by administering a therapeutically effective amount of a sensory stimulus to the person, where the sensory stimulus includes a two or more sensory stimuli patterns, including a first sensory stimuli including simultaneously providing a left visual stimuli pattern to the left eye of the user and a right stimuli pattern to the right eye, and a second sensory stimuli including simultaneously providing a right auditory stimuli pattern to the right side of a head of the user and a left auditory stimuli pattern to the left side of a head of the user. One or more of the left auditory stimuli pattern or the right auditory stimuli pattern comprises a sequence of stimuli patterns including the first stimuli pattern, the second stimuli pattern, and the third stimuli pattern.

The pain being treated may be a nociceptive pain, which may include but is not limited to pain caused by fractures/severe injury, non-migraine headaches, dental pain, burns, post-surgery pain, osteoarthritis, or cancer pain. The pain may also be neuropathic in origin, which may include but is not limited to pain caused by fibromyalgia, diabetic neuropathy, post herpetic neuralgia, radiculopathy, phantom limb, multiple sclerosis, spinal cord injury and traumatic brain injury.

Further, the sensory stimuli may be provided by itself, or in conjunction with other non-pharmaceutical methods or devices, or in conjunction with pharmaceuticals.

In certain embodiments, the sensory stimuli are provided using devices and methods described in U.S. patent application Ser. No. 15/360,808 (the '808 patent application) and in U.S. patent application Ser. No. in 15/910,252 (the '252 patent application). The '808 and '252 patent applications are co-owned with the present patent application and are both herein included by way of incorporation in their entirety.

These features together with the various ancillary provisions and features which will become apparent to those skilled in the art from the following detailed description are attained by the method of the present invention, preferred embodiments thereof being shown with reference to the accompanying drawings, by way of example only, wherein:

BRIEF DESCRIPTION OF THE SEVERAL VIEWS OF THE DRAWING

FIG. 5 includes a table of specifications for the first time segment ("Segment A");

FIG. 6 includes a table of specifications for the second time segment ("Segment B");

FIG. 7 includes a table of specifications for the third time segment ("Segment C");

FIG. 12 illustrates a Visual Analog Scale for pain.

DETAILED DESCRIPTION OF THE INVENTION

Various embodiments described herein are directed to non-pharmaceutical methods of managing pain. The methods include administering a therapeutically effective amount of a sensory stimulus to the person, resulting in a reduction of the person's perception of pain, and/or an improvement in the person's tolerance for pain.

The sensory stimulus provided to the person as described herein is provided over a period of time and may, in certain embodiments, comprise two or more simultaneous stimuli, such as a visual stimuli and an auditory stimuli. In addition, each sensory stimuli may include a temporal sequence of sensory stimuli patterns, such as a sequence of stimuli having different frequencies, and/or a stimuli that alternates between sensory organs, as by alternating between the eyes or ears or the person. In various embodiments, the stimulus may include, but is not limited to, one or more of: a visual stimuli to one or both eyes of the person; an auditory stimuli to one or both ears of the person; and/or a tactile stimuli to the skin of the person.

Figure 1:
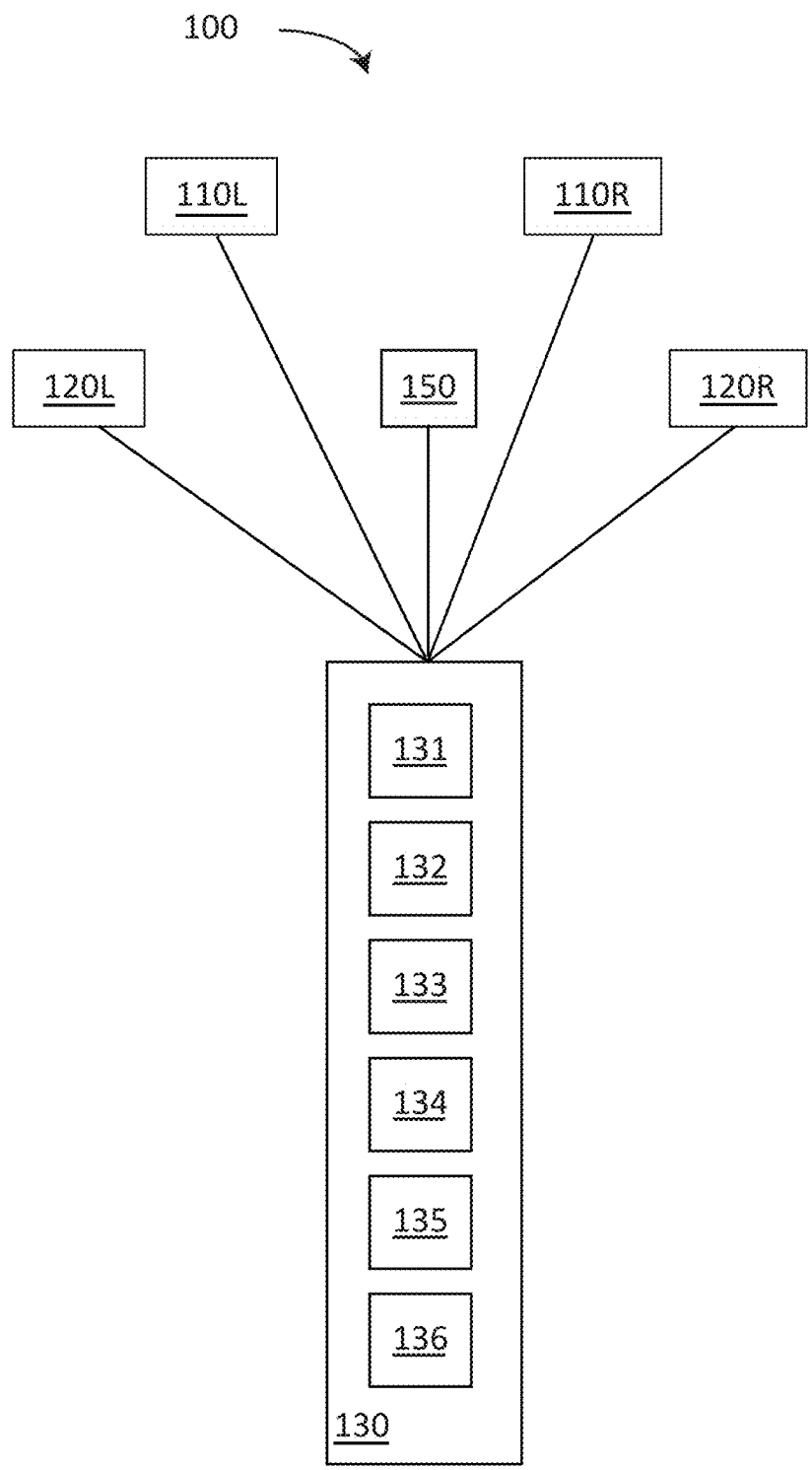
FIG. 1 is a schematic diagram of a system that may be used to provide a therapeutic sensory stimulus to a person.

FIG. 1 is a schematic diagram of a system 100 that may be used to provide a therapeutic sensory stimulus to a person. System 100 provides one or more stimuli outputs that a person wearing the system may experience as an auditory stimuli, a visual stimuli, and/or tactile stimuli. In one embodiment, system 100 comprises a left light source 110L, a right light source 110R, a left vibration source 120L, a right vibration source 120R, and a controller 130 for independently controlling and coordinating the action of the light and vibration sources. Thus, for example, system 100 may be positioned on the head of a user with left light source 110L positioned over the left eye to provide a left visual stimulus, right light source 110R positioned over the right eye to provide a right visual stimulus, left vibration source 120L positioned to provide left ear auditory stimuli, and right vibration source 120R positioned to provide right ear auditory stimuli.

In one embodiment, left and right light sources 110L, 110R may each comprise light-emitting diodes, an incandescent light source having a wavelength filter, a fluorescent light source, a backlit LCD panel, or other light source configured to provide to the user light at a desired, predetermined wavelength or wavelength range.

In one embodiment, left and right vibration sources 120L, 120R may each comprise earbuds, miniature speakers, or other vibration sources that can provide auditory stimuli to a user. In certain other embodiments, left and right vibration sources 120L, 120R may comprise bone conduction transducers in the audible frequency range to provide vibrations to the user's skull bone that is sensed as auditory by the user's ear. Optionally, one or more of left and right vibration sources 120L, 120R may also produce vibrations that are sensed as tactile stimuli. Thus, for example, controller 130 may provide first signals to bone conduction transducers that vibrate or oscillate at a first frequency that can be interpreted by the user as auditory stimuli and may provide second signals at a second, lower frequency that can be interpreted as a tactile sensation by the user. In other words, bone conduction transducers may be adapted to provide both auditory and tactile stimulus to the user.

In certain embodiments, left and right vibration sources 120L, 120R provide output at specific one or more frequencies or a range of frequencies. In one embodiment, left and right vibration sources 120L, 120R are separately controlled to provide output at certain times and to not provide output at other times. Thus, for example, a vibration source may be programmed to provide an output as an amplitude modulated audio frequency of 256 Hz. Thus, in this example, the vibration source is the product of an audio frequency and a square wave.

In an alternative embodiment, left and right vibration sources 120L, 120R provide signals of slightly different frequencies to the left and right ear. This results in a binaural beats effect, wherein the person perceives a sound at a frequency that is the difference between the frequency in the right ear and the frequency in the left ear. Thus, for example, when a person is provided with a 200 Hz audio frequency to the left ear and a 210 Hz audio frequency to the right ear, the person will perceive 200 Hz in the left ear, 210 Hz in the right ear, and 210 Hz–200 Hz=10 Hz which appear as being provided to both ears. One skilled in the art may use this effect to provide sound at brain wave frequencies separately from, or in combination with, the other methods described herein.

System 100 also includes a sensor assembly 150 that obtains one or more measurements from the user. Thus, for example and without limitation, sensor 150 may include, or is in communication with, a sensor that measures some property or characteristic of the user, including but not limited to, heart rate, heart rate variability, body temperature, or blood pressure, and includes electronics that provide a signal indicative of the measurement to controller 130. In other embodiments, the sensors are connected to sensor assembly 150 by wired or wireless connectors. Thus, in various embodiments, the sensors may include one or more: electrodes for sensing electrical activity in the brain, as in a 2 or 4 lead EEG, a temperature sensor, and/or a heartbeat sensor, or one or more EMG sensors positioned, for example and without limitation, to measure eye movement to ascertain when REM sleep is reached, and/or to measure muscle tone to aid in determining states of relaxation. In certain embodiments, controller 130 utilizes the signal from sensor assembly 150 to modify the intensity and/or timing of the light and vibration sources.

In one embodiment controller 130 includes: an output 131 to provide signals to actuate light sources 110L and 110R, vibration sources 120L and 120R, and any other components that provide sensory input to the user; an input 132 to accept signals from sensor assembly 150; a non-transitory memory 133 for storing programming and data for system 100; a processor 134; and a communications module 135. Memory 133 includes instructions that are accessible to processor 134 for operating the components that provide sensory input to the user, including but not limited to light sources 110L and 110R, vibration sources 120L and 120R, including accepting input provided to input 132 and modifying signals provided to components that provide sensory input to the user, including but not limited to light sources 110L and 110R, vibration sources 120L and 120R. Communications module 135 provides for the transfer of information to or from controller 130 by wired or wireless means.

In an alternative embodiment, system 100 may also provide tactile stimulus to a user by including a left tactile stimulus source and a right tactile stimulus source (not shown), each of which may be individually controlled and coordinated with the controller 130 to provide tactile stimuli to a user of therapeutic system 100.

Figure 2A:
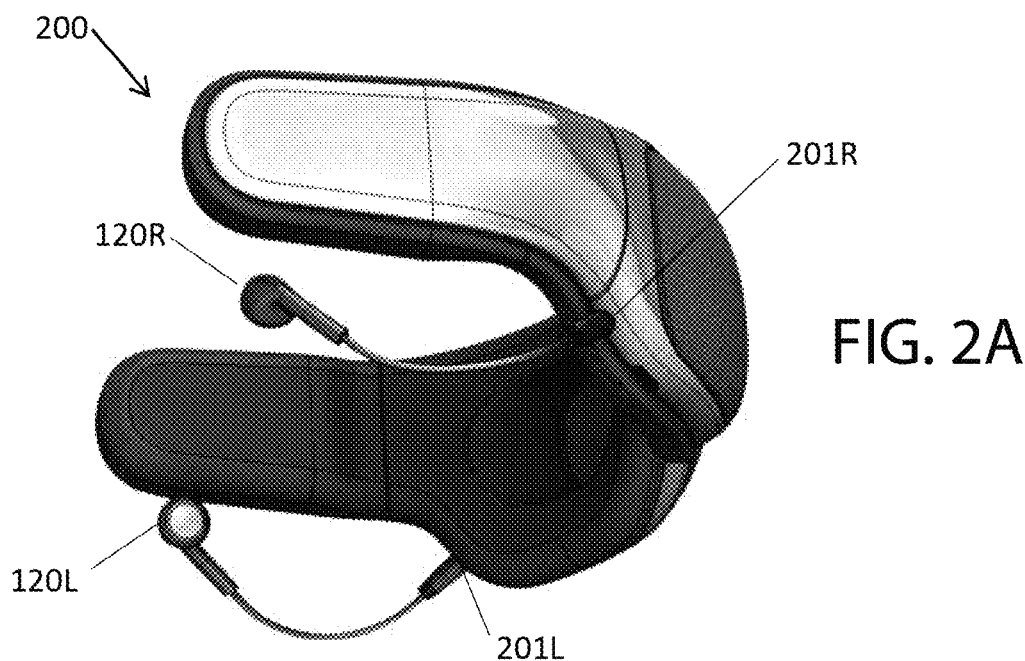
FIG. 2A, FIG. 2B, and FIG. 2C are a bottom right perspective view, a rear view, and a left view, respectively, of an embodiment of a headset.
Figure 2B:
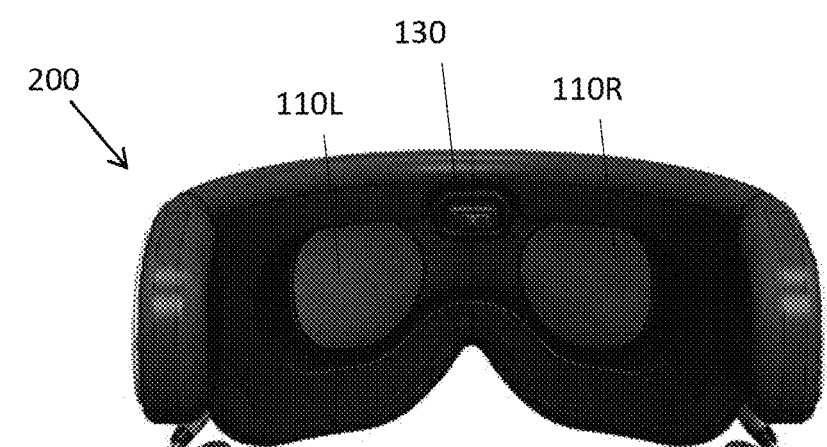
Figure 2C:
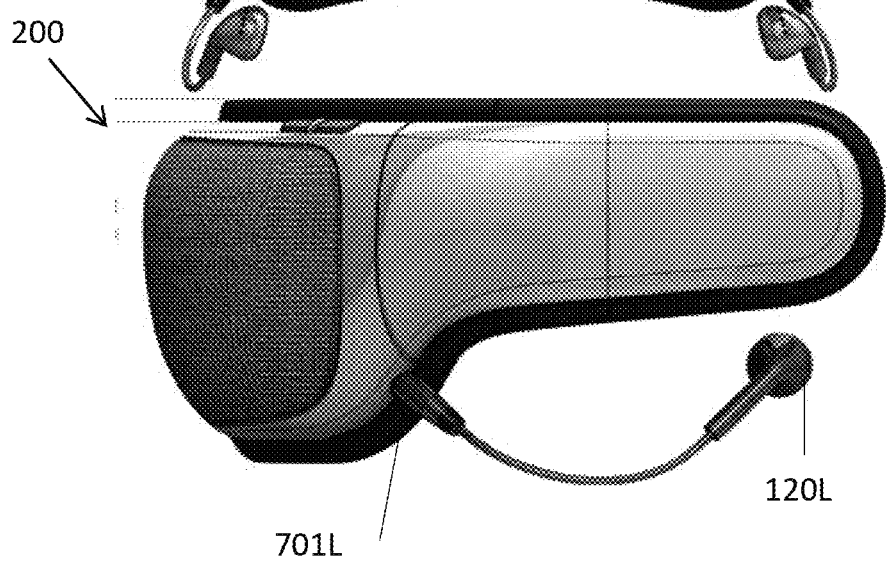
Figure 3:
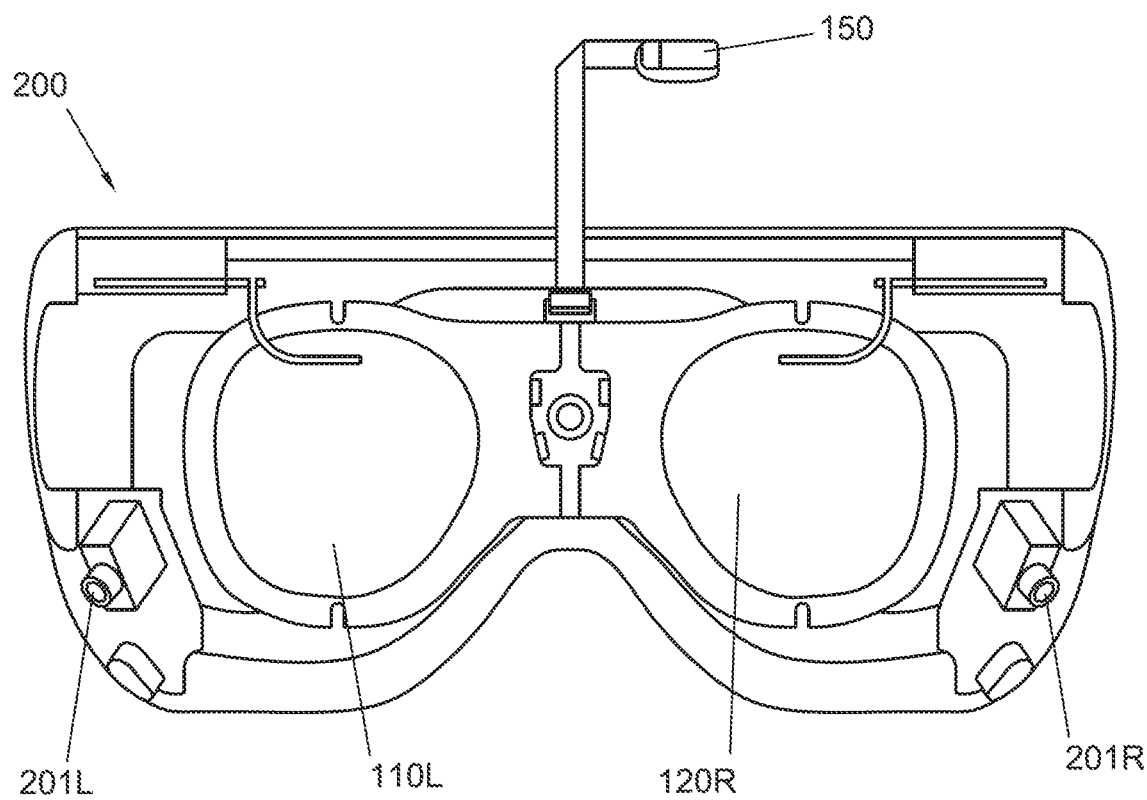
FIG. 3 is an exploded front view of the headset of FIGS. 2A-2C.

FIGS. 2A, 2B, and 2C are a bottom right perspective view, a rear view, and a left view, respectively, and FIG. 3 is an exploded front view, of headset 200, which is generally similar to system 100 except as explicitly noted.

Headset 100 includes sensor assembly 150, controller 130, light sources 110L and 110R, and vibration sources 120L and 120R. Sensor assembly 150 also includes a biometric sensor system, such as that which is sold under the name of VALENCELL BENCHMARK™ (Raleigh, N.C.), that includes an infrared light source and detector, which can be used to detect heart rate using pulse oximetry, an accelerator, and a processing unit. Sensor assembly 150 includes a sensor module circuit board that contains a digital optical detector system. This detector controls the LEDs and converts the optical signals reflected from the user's skin to digital format and communicates over the internal I2C bus to the PerformTek® processor. The accelerometer is also read via the internal I2C bus for activity signal.

In one embodiment, controller 130 includes a Nordic Semiconductor ASA (Oslo, Norway) model NRF51822 Multiprotocol BLUETOOTH® low energy/2.4 GHz RF System on Chip, and a VLSI Solution (Tampere, Finland) model VS1000 audio module.

In one embodiment, light sources 110L and 110R are Lite-On, Inc. (Milpitas, Calif.) Bin G3/W2/AU model LTST-020VSKT LEDS. In one embodiment, vibration sources 120L and 120R are Basen Technology Co, Ltd model PN: OEM-E170a earbuds.

In one embodiment, sensor assembly 150 also includes a PerformTek® processor which polls sensor data over the internal I2C bus and converts the raw measurements into data registers of biometric values (i.e. Heart Rate, Cadence, VO2) and processes those values further into higher level user assessments (i.e. Calories Burned, Distance, VO2 max, fitness level, and the period between heart rate beats (the Heart Rate Interval, or RR Interval)). The PerformTek® processor runs algorithms to convert the raw signals to a register array of biometric values and high-level assessments. These values are available for reading via the UART or I2C firmware interface. In addition, sensor module diagnostics such as signal quality, error codes, and serial number ID are available.

Sensor assembly 150 further includes control lines for interfacing controller 130 with the PerformTek® processor include a Power On Self-Test (POST), UART or I2C communication interface, and a wake-from-standby line (WAKE). The host processor can control much of the functionality of the sensor module via a software protocol interface over the UART or I2C interface.

In one embodiment, sensor assembly 150 determines a current heart rate, and/or an inter-beat R-R interval which is provided to controller 130. In another embodiment, sensor assembly 150 also provides accelerometer data to controller 130.

In yet another embodiment, sensor assembly 150 includes one or more EEG sensors, as are known in the field, and provides brain electrical activity measurements to controller 130.

In another embodiment, sensor assembly 150 includes one or more EMG sensors positioned, for example and without limitation, to measure eye movement to ascertain when REM sleep is reached, and/or to measure muscle tone to aid in determining states of relaxation. EMG sensors, as are known in the field, and provides brain electrical activity measurements to controller 130.

Headset 200 also includes left and right audio jacks 101L and 101R into which left and right earbuds 120L and 120R, respectively, may be plugged into. Alternatively, stereo headphones (not shown) may be plugged into one of jacks 101L or 101R, where the jacks are appropriately programmed to provide stereo sound to the headphones.

Figure 4:
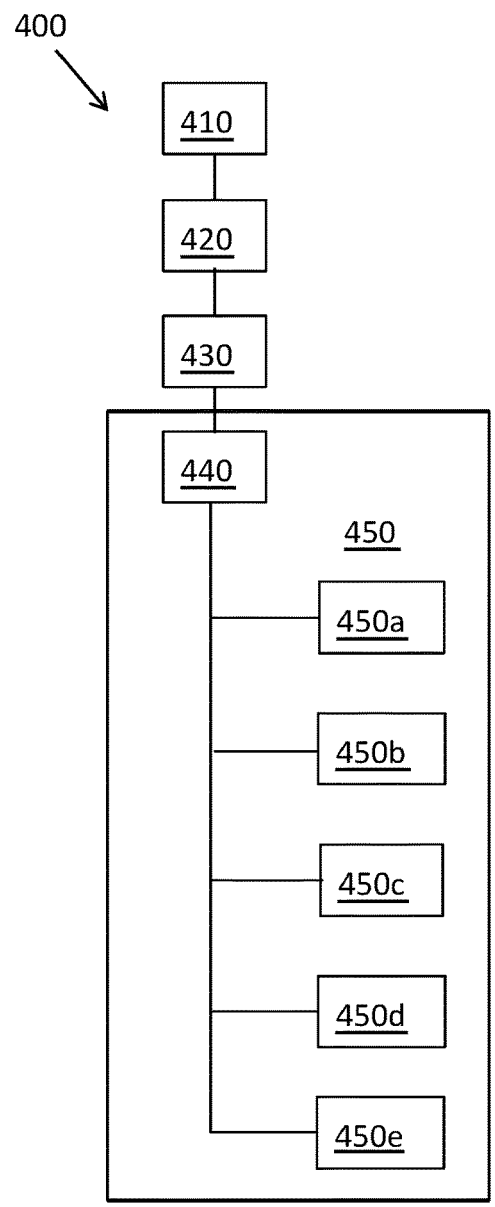
FIG. 4 is a flow chart of an exemplary method for providing therapeutic auditory, visual, and/or tactile stimulus.

FIG. 4 shows a flow chart of an exemplary method 400 for providing therapeutic auditory, visual, and/or tactile stimulus using, for example and without limitation, one of system 100 or headset 200. In a step 410, a subject having pain, or who wishes to undergo a treatment for managing pain, is identified. In a step 420, the subject is provided the therapeutic system or headwear, such as headset 200 as described above, and in step 430, the subject places the headset on their head. In a step 440, headset 200 executes programming 450 provided in controller 130 to provide stimuli to the subject. The programming provides two or more of auditory, visual, and/or tactile stimulus to the subject, and thus, for example, may provide power to activate left light source 110L, right light source 110R, left vibration source 120L and or right vibration source 120R. The programming also includes modifying the auditory, visual, and/or stimuli in response to measurements obtained by sensor assembly 150 and provided to controller 130.

As discussed above and herein, the left vibration source 120L and the right vibration source 120R may each comprise bone conduction transducer that may provide both auditory and tactile stimulus.

In certain embodiments, providing two or more of auditory, visual, and/or tactile stimulus concurrently may provide improved therapeutic benefits as compared to providing only one of auditory, visual, or tactile stimulus at one time. The two or more auditory, visual, and/or tactile stimulus may thus combine to provide the improved therapeutic benefits, for example (i.e., the two or more auditory, visual, and/or tactile stimulus may synergize in a way to provide improved results over providing two of the stimuli individually.)

Exemplary instructions for providing stimuli may be provided, for example, by programming 450, which includes one or more subroutines. One such subroutine is subroutine 450e, which analyzes measurements obtained from sensor assembly 150 and stores the analyzed measurements in memory 113. Subroutine 450a includes instructions for the simultaneous activation of all active auditory, visual, and/or tactile stimulus sources. Optionally, the activation of all sources may include the activation of tactile stimulation to run throughout all subsequent auditory and/or visual stimulation. Another exemplary subroutine 450b may include instructions for alternating the left auditory, visual, and/or tactile stimulus sources with the right auditory, visual, and/or tactile stimulus sources (i.e., the left stimuli and right stimuli take turns being active). Another exemplary subroutine 450c may include instructions for alternating the visual sources with the auditory and/or tactile sources (i.e., the visual stimuli and the auditory/tactile stimuli take turns being active). Another exemplary subroutine 450d may include instructions for alternating the left auditory and/or tactile source and the right visual source with the right auditory and/or tactile source and the left visual source (i.e., opposite auditory/tactile stimuli take turns being active).

In certain optional embodiments, one or more of subroutines 450a, 450b, 450c, or 450d, access the analyzed measurements from subroutine 450e and modifies the instructions they provide to the auditory, visual, and/or tactile stimuli depending on real-time or near real-time measurements of the user obtained from sensor assembly 150. Such programming is further described below.

In step 440, programming 450, including by not limited to subroutines 450a, 450b, 450c, and 450d, may each be applied one or more times, individually or in combination with one another. The programming may, in addition, provide sequences of output in subroutines 450a, 450b, 450c, and 450d at different frequencies and/or timings. Thus, for example the subroutines may provide output at specific frequencies that change as the subroutine is repeated.

In certain embodiments, the pulses that determine the amplitude modulation above are essentially square waves and thus, as determined by a Fourier analysis, are formed of sinusoidal components at the pulse frequency and at higher harmonics. As an approximation, an ideal square wave with a pulse frequency of P contains only odd-integer harmonic frequencies at $(2k-1)*P$, where $k=1, 2, 3 \ldots$, which contain a fraction $(2/\pi)/(2k-1)$ of the total power in the square wave. Thus, for example, the signal power in a square wave with a pulse frequency of 4 Hz includes a 63% of the power at 4 Hz, 21% of the power at 12 Hz, 13% of the power at 20, etc., If the square wave does not have equal on and off periods, then the pulse frequency will also contain even-integer harmonic frequencies.

Thus, for example, subroutine 450a may provide amplitude modulated auditory output to vibration source 120R or 120L at a carrier audio frequency of 256 Hz that is turned on and off, that is it is pulsed, at a pulse frequency of 1 Hz for 2 minutes, or may provide amplitude modulated light output to light source 110R or 110L that produces at a carrier light wavelength 580 nm that is turned on and off, that is it is pulsed at a at a pulse frequency of 1 Hz for 2 minutes. This square pulse auditory or light signal thus generates signals at a frequency of 1 Hz in addition to higher harmonics.

In certain embodiments, the subroutines described herein generate pulses having sinusoidal components that correspond with certain known brain wave frequencies, which are generally accepted as being delta waves (0.1 to 4.0 Hz), theta brain waves (4 to 7 Hz), alpha brain waves (8 to 15 Hz), beta waves (16 to 31 Hz), and gamma brain waves (32 to 100 Hz). Thus, certain embodiments include pulse frequencies of from 3.75 Hz to 4.25 Hz (theta brain waves), of from 1.25 Hz to 1.75 Hz (delta waves), and/or from 0.25 Hz and 0.75 Hz (delta waves).

In addition, by alerting the output between left and right channels, the brain may be stimulated in a way that it is forced to communicate between the left and right sides of the brain. This forced communication, for example, can allow PTSD memories to be wired to both sides of the brain, thereby stopping undesirable flashbacks. It can also create an enhanced relaxation effect, allowing for deeper relaxation and pain management.

In one embodiment, system 100 provides a stimulus that includes visual and auditory stimuli over three temporally sequential segments—a first segment where stimuli occurs at a first frequency, followed by a second segment where stimuli occurs at a second frequency, which was followed by a third segment where stimuli occurs at a third frequency. Each time segment included sub-segments of visual and auditory stimuli, where each sub-segment was determined by one of the subroutines described above, for example. The visual stimuli were provided by pulsing light at a wavelength of 580 nm at certain pulse frequencies and by pulsing auditory signals at a frequency of 256 Hz at certain pulse frequencies.

In one embodiment, a treatment stimulus lasted for 16 minutes, and may be understood by reference to Table 500 in FIG. 5, Table 600 in FIG. 6, and Table 700 in FIG. 7, where Table 500 contains specifications for the first segment ("Segment A"), Table 600 contains specifications for the next, second time segment ("Segment B"), and Table 700 contains specifications for the last time segment ("Segment C"). Each of the Segments stimuli patterns at a different pulse frequency. Specifically, Segment A cycles the stimuli through a block of four Segment A stimuli patterns for a total of 2 minutes, Segment B cycles the stimuli through a block of four Segment B stimuli patterns for a total of 2 minutes, and Segment C cycles the stimuli through a block of six Segment C stimuli patterns for a total of 12 minutes.

More specifically, in the four Segment A stimuli patterns, as shown in Table 500 as Blocks A1, A2, A3, and A4 respectively, the auditory and light outputs cycle 115 or 116 times between being on for 0.1277 seconds and then being off for 0.1277 seconds (that is, at a pulse frequency of 3.9 Hz), followed by no output for 0.5 seconds. In the Segment B stimuli patterns, as shown in Table 600 as Blocks B1, B2, B3 and B4, the auditory and light outputs cycle 44 or 45 times between being on for 0.3333 seconds and then being off for 0.3333 seconds (that is, at a pulse frequency of 1.5 Hz) followed by no output for 0.5 seconds. In the Segment C stimuli patterns, as shown in Table 700 and labeled Blocks C1, C2, C3 and C4, the auditory and light outputs cycle 14 or 15 times between being on for 1 second and then being off for 1 second (that is, a pulse frequency of 0.5 Hz), followed by no output for 1 second. Blocks A1, B1, and C1 pulse the right and left sides of both the light and auditory together, with all outputs are synchronized to be on or off at the same time, as provided by subroutine 450a. Blocks A2, B2, and C2 synchronize the left side light and auditory output, and the right side light and auditory output to be opposite to one another, as provided by subroutine 450b.

Blocks A3, B3, and C3 synchronize both lights together to be opposite to both auditory outputs, as provided by subroutine 450c. Blocks A4, B4, and C4 synchronize the right auditory and light to be opposite to the left auditory and light outputs, as provided by subroutine 450d.

In step 440, subroutine 450e receives measurements from sensor assembly 150 and stores analyzed measurements. In one embodiment, sensor assembly 150 provides instantaneous, or nearly instantaneous, measurements from the user. Thus, for example and without limitation, sensor assembly 150 provides a sequence of measurements of beat-to-beat intervals of the heart of the user, that is, the time interval between the last two heart beats, which is also referred to, without limitation, as the RR intervals. Controller 130 then computes and stores values of the heart rate variability (HRV), which is a mathematical representation of the physiological phenomenon of variation in the time interval between heartbeats.

In certain embodiments, a time-domain calculation of RR intervals, as obtained by sensor assembly 150, is used to compute the HRV. Thus, for example, the sequence of RR intervals ("$RR_i$") is accepted from sensor assembly 150 and stored in memory 133. After the accumulation $RR_i$ for a period of time, T, the HRV is calculated as approximated by the root mean square of successive differences between adjacent RRs, or RMSSD. Thus, at a time T from the beginning of the accumulation of data, if N consecutive RR intervals are stored in memory 133, the following calculation is performed in processor 134 according to a program stored in the memory:

$$RMSSD = \sqrt{\frac{1}{N-1}\left(\sum_{i=1}^{N-1}(RR_{i+1} - RR_i)^2\right)}$$

The initial value of RMSSD (that is, $RMSSD_0$) is stored in memory 133 as a baseline. Thereafter, at the end of each period T, the calculation of RMSSD is repeated covering that time period. As a result, a sequence of $RMSSD_j$ values are computed. Next the difference between the current RMSSD value and the baseline $RMSSD_0$ is computed as $\Delta RMSSD_j = RMSSD_j - RMSSD_0$. $\Delta RMSSD$ is a measure of the change between the current HRV and the baseline, initial HRV.

In general, it is realized by those skilled in the art, that an increased in HRV is associated with a relaxed state, or a sleep state, and that a decrease in HRV is associated with a less relaxed, or stressed, state. For uses of therapeutic system 100 intended to calm a person or to induce sleep, a positive $\Delta RMSSD$ indicates that the person is becoming relaxed and that the system is working as intended. A negative $\Delta RMSSD$ indicates that the person is not becoming more relaxed. In one embodiment, an indication that the person is relaxed ($\Delta RMSSD > 0$) is used to modify the treatment by reducing the treatment time and/or intensity of the stimuli, and an indication that the person is less relaxed ($\Delta RMSSD < 0$) is used to modify the treatment to increase the treatment time and/or the intensity of the stimuli.

In certain embodiments, Kubios HRV software (manufactured by Kuopio, Finland) is used to analyze the RR intervals to provide additional HRV related data. Thus, for example, one useful measure for analyzing HRV is the fraction of the power of the HRV signal that occurs in certain frequency ranges. Thus, for example, one measure which is referred to herein as HRV-HFnu is obtained by taking the Fourier transform of the HRV signal and computing the ratio of the power of the HRV signal from 0.15 to 0.40 Hz ("high frequencies") to the total power of the HRV signal The calculations described above are provided by way of explanation and are not meant to limit the scope of the calculations or how the operation of therapeutic system 100 is or is not modified using HRV measurements.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, circuitry of the controller 130 or the external control unit 130a such as one or more of a processor or logic circuitry such as a central processing unit (CPU) or a programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

Subjective and Objective Measures

In the examples discussed subsequently, test subjects were provided with a number of sensory stimuli and their response to the treatment was determined using objective and subjective measures.

The objective measure is derived from the subject's HRV. Specifically, the RR intervals are used to calculate the HRV, as discussed above, which are then used to compute HRV-HFnu.

Subjective measures were obtained by a survey, referred to herein as a Visual Analog Scale ("VAS"), that the person completed just before and just after a placebo stimulus or a treatment stimulus. FIG. 12 illustrates a VAS 1200 that was presented to the subjects to assist in the determination of levels of pain, relaxation, and anxiety. Specifically, the VAS surveys used included: 1) a Pain VAS, in which subjects rate their perceived level of pain as being between "No Pain," which is assigned a value of zero, and "Worst Pain Imaginable," which is assigned a value of 10; 2) a Relaxation VAS, in which subjects rate their perceived level of relaxation as being between "Most Relaxed," which is assigned a value of zero, and "Least Relaxed/Stressed," which is assigned a value of 10; and 3) an Anxiety VAS, in which subjects rate their perceived level of anxiety as being between "Not at all anxious," which is assigned a value of zero, and "Very anxious," which is assigned a value of 10.

EXAMPLE 1

One study was performed on 75 volunteer participants. This included 24 people with chronic pain/insomnia: 18 highly trained military personnel and 6 professional hockey players all of whom exhibited some degree of chronic pain and sleep issues; and 27 people without chronic pain or sleep issues (referred to herein as "normal" people): 21 with varying levels of acute pain from, for example, short term lower back pain or a knee injury and 6 people with no pain reported. The participants were, at the time of the study, experiencing pain from one or more of a number of sources, including fibromyalgia, mild traumatic brain injury (mTBI), traumatic brain injury (TBI), ankle sprain, frozen shoulder, meniscus tear of shoulder, burns, neuropathic pain, sciatica, premenstrual syndrome (PMS), and arthritis rheumatoid and osteoarthritis.

The study procedure included providing each participant with headset 200 and allowing them to sit reclined in an armchair, with a blanket to keep warm if requested. By way of a clinical trial, headset 200 was programmed to provide the participants with two rounds of stimulus: a placebo stimulus and a treatment stimulus, in an order that was randomly selected. For the placebo stimulus, the participants were provided with headset 200 which provided the participants with a continuous light and sound exclusion (sensory deprivation). For the treatment stimulus, the participants were provided with 16 minutes of a regimen comprising auditory and visual stimuli. Data collected immediately before and before and after each round of stimuli included a pain VAS survey, a relaxation VAS survey, and HRV-HFnu as determined from HRV measurements.

The effectiveness of the treatment performed in this Example was determined by comparing, for each participant, the data obtained from the placebo stimulus with that of the treatment stimulus. The visual stimuli were provided by pulsing light at a wavelength of 580 nm at certain pulse frequencies and by pulsing auditory signals at a frequency of 256 Hz at certain pulse frequencies. The treatment stimulus lasted for 16 minutes, as described above with reference to Tables 500, 600, and 700.

Figure 8:
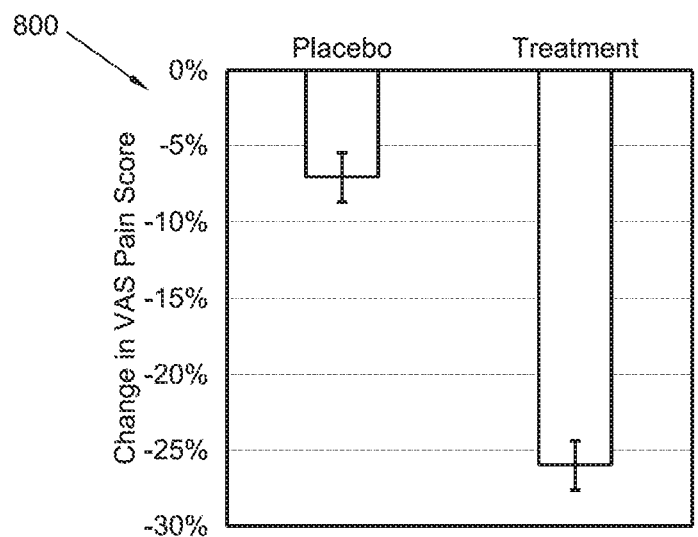
FIG. 8 presents results related to pain relief.
Figure 9:
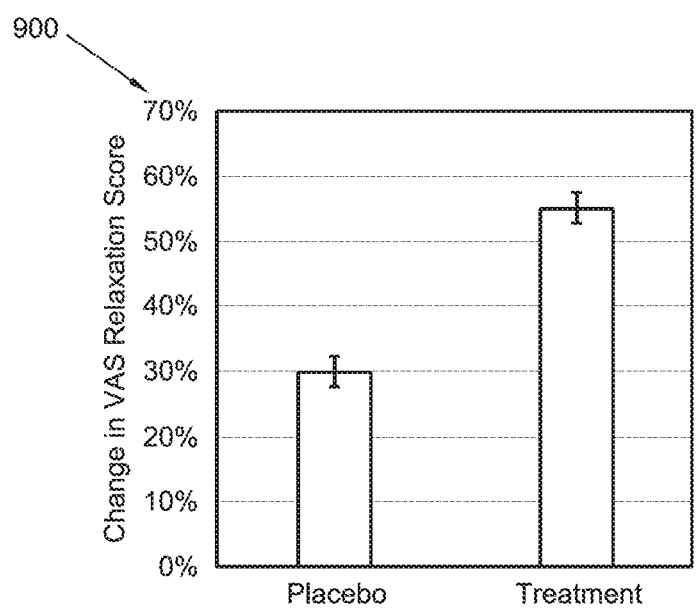
FIG. 9 presents results for relaxation.
Figure 10:
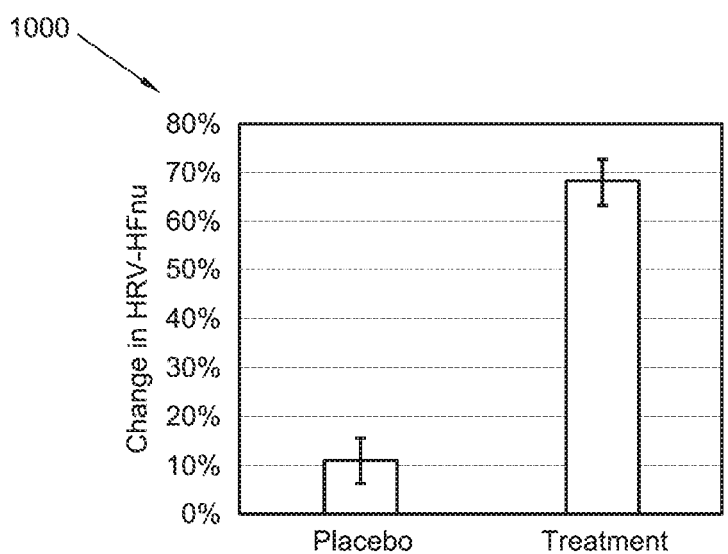
FIG. 10 presents results from HRV measurements.

The results from this Example are presented in FIGS. 8-10, where FIG. 8 presents results related to pain relief, FIG. 9 presents results for relaxation, and FIG. 10 presents results from HRV measurements.

FIG. 8 includes a graph 800, which includes a comparison of the subjective measure of pain using the Pain VAS. Specifically, for each placebo round and treatment round, the difference in VAS score for pain was computed—that is, for all 75 participants, the change in VAS score was calculated for each placebo round and each treatment round. The results in graph 800 show the average difference in the pain scores, along with the standard error of the mean, for all participants undergoing a placebo round and a treatment round. For participants undergoing a placebo round there was an average decrease of 7% in pain, and for all participants undergoing a treatment round there was an average decrease of 26%, in pain, where the statistical measures are $P(T \leq t)$ two-tail $P=0.003$. The results shown that the treatment was 3.7 times more effective at reducing the subjective measure of pain than was the placebo.

FIG. 9 includes a graph 900, which includes a comparison of the subjective measure of relaxation using the Relaxation VAS. Specifically, for each placebo round and treatment round, the difference in VAS score for relaxation was computed—that is, for all 75 participants, the change in VAS score was calculated for each placebo round and each treatment round. The results in graph 900 show the average difference in the relaxation scores, along with the standard error of the mean, for all participants undergoing a placebo round and a treatment round. For participants undergoing a placebo round there was an average increase of 30% in relaxation, and for all participants undergoing a treatment round there was an average increase of 55%, in relaxation, where the statistical measures are $P(T \leq t)$ two-tail $P=1 \times 10^{-9}$. The results shown that the treatment was nearly twice as effective at increasing the subjective measure of relaxation than was the placebo.

FIG. 10 includes a graph 1000, presents values of HRV-HFnu, as measured for all 75 participants. Specifically, the data in graph 1000 is average, for all participants, of the difference in HRV-HFnu for a placebo stimulus and for a treatment stimulus. The results in graph 1000 show the average increase in HRV-HFnu, along with the standard error of the mean, for all participants undergoing a placebo stimulus and a treatment stimulus. For participants undergoing a placebo stimulus there was an average increase of 11% in HRV-HFnu, and for all participants undergoing a treatment stimulus there was an average increase of 68%, in HRV-HFnu, where the statistical measures are $P(T \leq t)$ two-tail $P=0.003$. The results show that the treatment was more than six times as effective at increasing HRV-HFnu than was the placebo. The results in graph 1000 are consistent with other studies of HRV, which show a strong correlation between HRV-HFnu and a faster time for a person to go to sleep and for increased sleep quality.

EXAMPLE 2

A study was conducted on the effectiveness of the inventive method for treating symptoms of withdrawal to addictive drugs using a double-blind, randomized, controlled cross-over study of 8 subjects (for a total of 16 subject experiences). The subjects were patients of an inpatient treatment program in which they were receiving daily doses of 60-80 mg of methadone per day.

The study was conducted as follows. Each patient was taken off of methadone for one week to test the effectiveness of the inventive method. Within 12 hours of their last dose, baseline data was obtained using several VAS surveys. The results presented here are the Pain VAS and the Anxiety VAS.

During the first full day without methadone, each patient received several rounds of stimuli, which was either several rounds of a treatment stimulus, as described above with reference to Tables 500, 600, and 700. or several rounds of a placebo stimulus, as described above. The stimuli were provided with headset 200 five times during a 16-hour awake period, starting at 8:00, with the last treatment prior to bedtime [e.g., approximately 08:00, 12:00, 16:00, 20:00, and 22:00-24:00]). Subjects were allowed to request additional treatments, provided the treatment sessions do not interfere with the planned sessions or other assessments.

At the end of a day in which multiple rounds of treatment stimuli or multiple rounds of placebo stimuli had been administered to the subjects, the VAS surveys were repeated.

A rest period of at least 7 days was provided between the treatment and placebo rounds, during which the subjects took their normal dosage of methadone to allow for a return to steady-state methadone levels between data collection phases.

Figure 11:
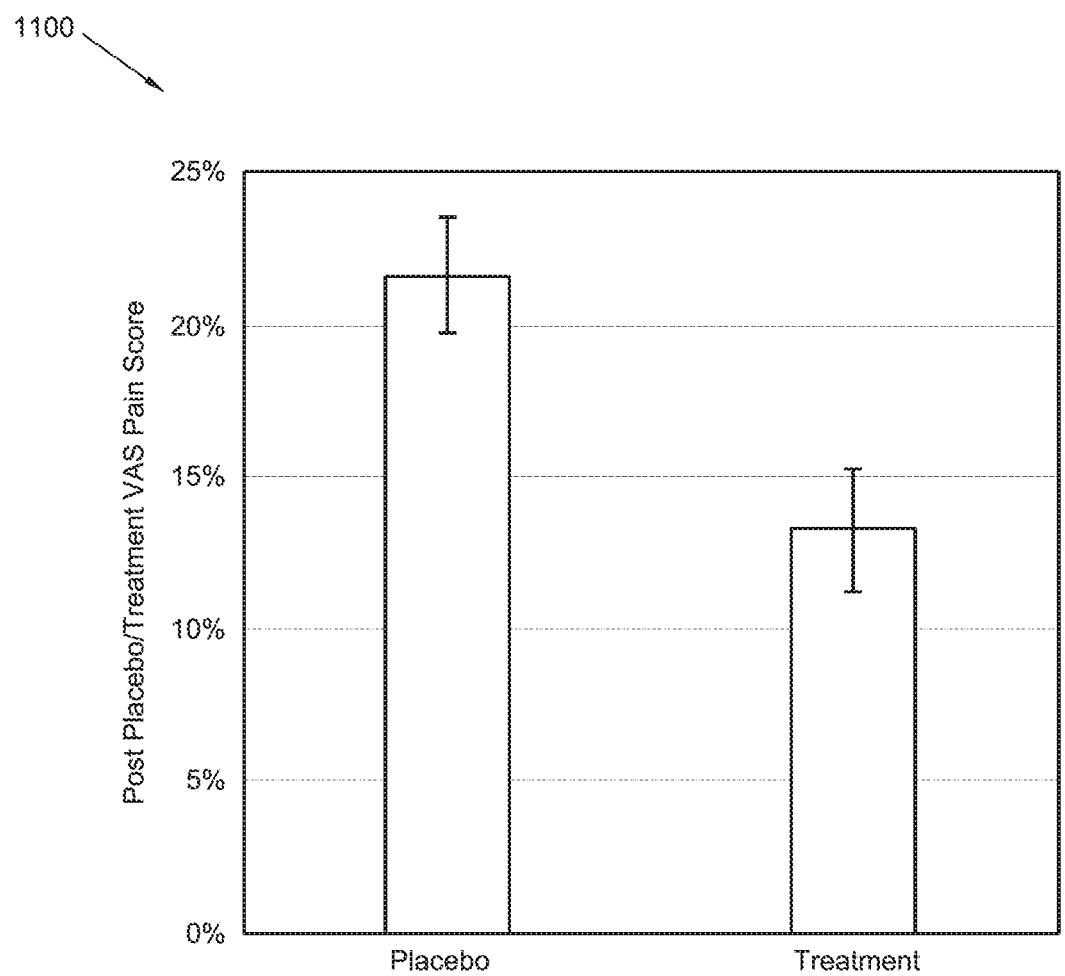
FIG. 11 includes a graph that compares the subjective measure of pain for all test subjects that were provided first with a treatment stimulus, followed by a placebo stimulus.

FIG. 11 includes a graph 1100, which includes a comparison of the subjective measure of pain using the Pain VAS for all test subjects that were provided first with a treatment stimulus, followed by a placebo stimulus. The results in graph 1100 show that for a placebo stimulus, the average Pain VAS for all subjects was 20.0, while for a treatment stimulus the average Pain VAS for all subjects was 5.7, which is 3.5 times less than the pain of subjects receiving a placebo, with a value of $P=0.001$.

Further, anecdotal results of the inventive method indicate that the method is effective at treating brain stem stroke, persistent vegetative state, migraine, trauma induced headache, oncology pain, unstable angina, trigeminal neuralgia, tension headaches, whiplash, Crohn's disease, spinal cord injury, tendonitis, carpal tunnel syndrome, lupus, and Raynaud's syndrome.

One embodiment of each of the methods described herein is in the form of a computer program that executes on a processing system, e.g., a one or more processors that are part of a system 100. Thus, as will be appreciated by those skilled in the art, embodiments of the present invention may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code segments embodied in the medium. Any suitable computer readable medium may be used including a magnetic storage device such as a diskette or a hard disk, or an optical storage device such as a CD-ROM.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

What is claimed is:

1. A method of managing pain, said method comprising administering a therapeutically effective amount of a sensory stimulus to a person, wherein:
   said sensory stimulus includes one or more of a visual stimuli and an auditory stimuli; and
   said sensory stimulus includes alternating between
      a first sensory stimuli including providing simultaneously a first visual stimuli pattern to an eye on a first side of a head of the person and a first auditory stimuli pattern to an ear on a second side of the head, and
      a second sensory stimuli including providing simultaneously a second visual stimuli pattern to an eye on the second side of the head and second auditory stimuli pattern to an ear on the first side of the head.

2. The method of claim 1, wherein the pain includes a nociceptive pain.

3. The method of claim 2, wherein said nociceptive pain is pain caused by one or more of a fracture, a severe injury, a nonmigraine headache, a dental pain, a burn, post-surgery recovery, and osteoarthritis.

4. The method of claim 1, wherein the pain includes a neuropathic pain.

5. The method of claim 4, wherein said neuropathic pain is pain caused by fibromyalgia, diabetic neuropathy, post herpetic neuralgia, radiculopathy, phantom limb, multiple sclerosis, spinal cord injury, and traumatic brain injury.

6. The method of claim 1, wherein said pain is a chronic pain.

7. The method of claim 1, wherein administering the therapeutically effective amount of the sensory stimulus to the person reduces the person's perception of pain.

8. The method of claim 7, wherein said person's perception of pain is less than one third of the person's perception of pain in comparison to administering visual and auditory sensory deprivation for an amount of time equal to that of administering the therapeutically effective amount of the sensory stimulus to the person.

9. The method of claim 1, wherein administering the therapeutically effective amount of the sensory stimulus to the person improves the person's tolerance for pain.

10. The method of claim 1, wherein said visual stimuli includes an amplitude modulated light source.

11. The method of claim 1, wherein one of said one or more visual stimuli includes a sinusoidally varying light source.

12. The method of claim 1, wherein one of said one or more said auditory stimuli includes an amplitude modulated audio frequency.

13. The method of claim 1, wherein:
   said sensory stimulus includes two or more sensory stimuli patterns including a first stimuli pattern that is different than a second stimuli pattern;
   said first stimuli pattern includes a sinusoidal component that is between 3.75 Hz and 4.25 Hz, is between 1.25 Hz and 1.75 Hz, or is between 0.25 Hz and 0.75 Hz; and
   said second stimuli pattern includes a sinusoidal component that is between 3.75 Hz and 4.25 Hz, is between 1.25 Hz and 1.75 Hz, or is between 0.25 Hz and 0.75 Hz.

14. The method of claim 13, wherein said two or more stimuli patterns includes a third stimuli pattern that is different than said first stimuli pattern and said second stimuli pattern.

15. The method of claim 14, wherein:
   said first stimuli pattern includes a sinusoidal component that is between 3.75 Hz and 4.25 Hz, is between 1.25 Hz and 1.75 Hz, or is between 0.25 Hz and 0.75 Hz;
   said second stimuli pattern includes a sinusoidal component that is between 3.75 Hz and 4.25 Hz, is between 1.25 Hz and 1.75 Hz, or is between 0.25 Hz and 0.75 Hz; and
   said third stimuli pattern includes a sinusoidal component that is between 3.75 Hz and 4.25 Hz, is between 1.25 Hz and 1.75 Hz, or is between 0.25 Hz and 0.75 Hz.

16. The method of claim 1, wherein said sensory stimulus alternates between
   the first sensory stimuli including simultaneously providing a left visual stimuli pattern to a left eye of the person and a right auditory stimuli pattern to a right side of the head, and a second sensory stimuli including simultaneously providing a right visual stimuli pattern to a right eye of the person and a left auditory stimuli pattern to a left side of the head of the person,
wherein one or more of the left auditory stimuli pattern or the right auditory stimuli pattern comprises a sequence of stimuli patterns including the first stimuli pattern, the second stimuli pattern, and a third stimuli pattern.

17. The method of claim 16, further comprising:
periodically providing a sensory stimuli including simultaneously providing the left visual stimuli pattern to the left eye of the person, the right visual stimuli pattern to the right eye of the person, the left auditory stimuli pattern to the left side of the head, and the right auditory stimuli pattern to the right side of the head of the person.

18. The method of claim 16, further comprising:
alternating sensory stimuli between
   a third sensory stimuli including simultaneously providing the left visual stimuli pattern to the left eye of the person and the left auditory stimuli pattern to the left side of the head, and
   a fourth sensory stimuli including simultaneously providing the right visual stimuli pattern to the right eye of the person and the right auditory stimuli pattern to the right side of a head of the person.

19. The method of claim 16, further comprising:
alternating sensory stimuli between
   a fifth sensory stimuli including simultaneously providing the left auditory stimuli pattern to the left side of the head and the right auditory stimuli pattern to the right side of the head, and
   a sixth sensory stimuli including simultaneously providing the left visual stimuli pattern to the left eye of the person and the right visual stimuli pattern to the right eye of the person.

20. The method of claim 16, wherein the left auditory stimuli pattern comprises generating the left auditory stimuli pattern with a left speaker, and wherein generating the right auditory stimuli pattern comprises generating the right auditory stimuli pattern with a right speaker.

21. The method of claim 16, wherein the left auditory stimuli pattern comprises generating the left auditory stimuli pattern with a left bone conduction transducer of the headset, and wherein the right auditory stimuli pattern comprises generating the right auditory stimuli pattern with a right bone conduction transducer of a headset.

22. The method of claim 16, wherein one or more of the left or right auditory stimuli pattern includes an auditory frequency of from 240 Hz to 480 Hz.

23. The method of claim 16, wherein:
said two or more stimuli patterns include a first stimuli pattern having a first pulse frequency and a second stimuli pattern having a second pulse frequency; and
one or more of the left visual stimuli pattern or right visual stimuli pattern comprises repeatedly pulsing a light at one or more of the first pulse frequency, the second pulse frequency where the second pulse frequency is less than the first pulse frequency, and a third pulse frequency, where the third pulse frequency is less than the first and second pulse frequencies.

24. The method of claim 23, wherein the first pulse frequency is between 3.75 Hz and 4.25 Hz, the second pulse frequency is between 1.25 Hz and 1.75 Hz, and the third pulse frequency is between 0.25 Hz and 0.75 Hz.

25. The method of claim 16, wherein repeatedly pulsing the light comprises pulsing the light for a predetermined time interval.

26. The method of claim 25, wherein the predetermined time interval is 25-45 seconds.

27. The method of claim 16, wherein the sequence of stimuli patterns each have a pulse frequency having a pulse period, where a portion of the pulse period includes a stimulus of an auditory frequency of from 240 Hz to 480 Hz.

28. The method of claim 17, wherein said portion of said pulse period is one half of the pulse period.

29. The method of claim 16, wherein said first stimuli pattern, said second stimuli pattern, or said third stimuli pattern stimulates for a predetermined time interval.

30. The method of claim 29, wherein the predetermined time interval is 25-35 seconds.

31. The method of claim 30, wherein the predetermined time interval is 30 seconds.

32. A method of managing pain, said method comprising administering a therapeutically effective amount of a sensory stimulus to a person, said method comprising:
providing a headset to be worn by the person; and
administering, with the headset, the therapeutically effective amount of a sensory stimulus to the person, wherein said sensory stimulus includes one or more of a visual stimuli and an auditory stimuli and includes alternating between
   a first sensory stimuli including providing simultaneously a first visual stimuli pattern to an eye on a first side of a head of the person and a first auditory stimuli pattern to an ear on a second side of the head, and
   a second sensory stimuli including providing simultaneously a second visual stimuli pattern to an eye on the second side of the head and second auditory stimuli pattern to an ear on the first side of the head.

* * * * *